United States Patent
Quaka et al.

(10) Patent No.: US 10,583,031 B2
(45) Date of Patent: Mar. 10, 2020

(54) ANTI SNORING AND SLEEP APNEA DEVICE HAVING HERBST-MECHANISMS

(71) Applicants: Gary W Quaka, Ballwin, MO (US); Darren G. Buddemeyer, Frontenac, MO (US)

(72) Inventors: Gary W Quaka, Ballwin, MO (US); Darren G. Buddemeyer, Frontenac, MO (US)

(73) Assignee: ORTHO SOLUTIONS, LC, St. Ann, MO (US)

( * ) Notice: Subject to any disclaimer, the term of this patent is extended or adjusted under 35 U.S.C. 154(b) by 0 days.

(21) Appl. No.: 14/121,580

(22) Filed: Sep. 19, 2014

(65) Prior Publication Data

US 2015/0101614 A1 Apr. 16, 2015

Related U.S. Application Data

(60) Provisional application No. 61/961,469, filed on Oct. 14, 2013.

(51) Int. Cl.
*A61F 5/56* (2006.01)
*A61C 7/36* (2006.01)

(52) U.S. Cl.
CPC ............... *A61F 5/566* (2013.01); *A61C 7/36* (2013.01)

(58) Field of Classification Search
CPC ....... A61F 5/56–566; A61C 7/36; A61C 7/08; A63B 71/085; A63B 71/08; A63B 71/081; A63B 2071/086; A63B 2071/088
See application file for complete search history.

(56) References Cited

U.S. PATENT DOCUMENTS

| | | | |
|---|---|---|---|
| 3,761,452 A * | 9/1973 | Dawson | C08G 18/10 528/49 |
| 5,427,117 A | 6/1995 | Thornton | |
| 5,499,633 A | 3/1996 | Fenton | |
| 5,645,422 A | 7/1997 | Williams | |
| 5,769,631 A | 6/1998 | Williams | |
| 5,807,100 A * | 9/1998 | Thornton | A61C 9/00 128/862 |
| 5,919,042 A | 7/1999 | Williams | |
| 5,941,246 A | 8/1999 | Roopchand | |
| 6,036,488 A | 3/2000 | Williams | |
| 6,241,517 B1 | 6/2001 | Williams | |
| 6,247,926 B1 | 6/2001 | Thornton | |
| 6,402,510 B1 | 6/2002 | Williams | |
| 6,418,933 B1 * | 7/2002 | Strong | A61F 5/566 128/848 |
| 6,464,924 B1 | 10/2002 | Thornton | |
| 6,520,772 B2 | 2/2003 | Williams | |

(Continued)

*Primary Examiner* — Alireza Nia
*Assistant Examiner* — Michelle J Lee
(74) *Attorney, Agent, or Firm* — Lewis Rice LLC

(57) ABSTRACT

An anti-snoring and sleep apnea device is disclosed in which the device comprises an upper tray structure adapted for receiving upper teeth of a mouth of an individual, a lower tray structure adapted for receiving lower teeth of the mouth of the individual, a first Herbst mechanism connected to the upper tray structure and the lower tray structure, and a second Herbst mechanism connected to the upper tray structure and the lower tray structure, the first and second Herbst mechanisms for adjusting the position of the lower tray structure relative to the upper tray structure.

1 Claim, 2 Drawing Sheets

(56) References Cited

U.S. PATENT DOCUMENTS

| | | | |
|---|---|---|---|
| 6,719,557 B1 | 4/2004 | Williams | |
| 6,830,051 B1 | 12/2004 | Lesniak et al. | |
| 6,877,982 B2 | 4/2005 | Williams | |
| 7,094,051 B2 | 8/2006 | Williams | |
| 7,500,851 B2 | 3/2009 | Williams | |
| 2008/0149110 A1 | 6/2008 | Baldwin | |
| 2008/0149114 A1 | 6/2008 | Baldwin | |
| 2012/0070797 A1* | 3/2012 | Edgren | A61C 7/36 433/19 |
| 2013/0074848 A1* | 3/2013 | Metz | A61F 5/566 128/848 |
| 2013/0323668 A1* | 12/2013 | Ash | A61C 7/36 433/19 |

* cited by examiner

ANTI SNORING AND SLEEP APNEA DEVICE HAVING HERBST-MECHANISMS

CROSS REFERENCE TO RELATED APPLICATION

This non provisional patent application claims priority to U.S. Provisional Patent Application having Ser. No. 61/961,469, filed on Oct. 14, 2013, which claims priority to the provisional patent application having Ser. No. 61/854,898, filed on May 3, 2013, the disclosure of which is incorporated herein by reference.

FIELD OF THE DISCLOSURE

This disclosure generally relates to an anti-snoring and sleep apnea device that effectively can be adjustably manipulated to add pressure to force the lower jaw of the user to some extent forwardly relative to the upper jaw and thereby attain a sustained greater opening of the air passage, to reduce sleep apnea and related defects.

BACKGROUND

This disclosure generally relates to an anti-snoring and sleep apnea device, with improved structure to allow the device to be adjusted to various positions that allow for the maximum breathing by an individual, during it application.

There are a myriad of teeth, jaw and even various apnea devices that are available in the art. For example, there are many patents on various types' expansion means. Herbst type appliances and related types of structures are useful for adjusting the alignment, expansion or spread of teeth, or even the movement of one's jaw relative to the other, as when attempting to alleviate an overbite condition. Most of these devices are constructed for the purpose of providing orthodontic benefits to the patient, so as to correct the misalignment of teeth, other structural defects in the arrangement of teeth and various jaws, relative to each other, so as to furnish a dental correction to either a birth defect, or genetic misalignment of teeth, or to maintain the alignment of teeth after their disruption or breakage as a result of an impact or accident.

Examples of these types of appliances may be seen in various patents to Williams, such as U.S. Pat. No. 5,645,422, which discloses a mandibular and maxillary arch expander. A similar type of expansion device can be seen in U.S. Pat. No. 5,769,631, on the orthodontic device as disclosed by Williams. U.S. Pat. No. 5,919,042, on a mandibular and maxillary arch expander and jaw repositioner, shows the application of the Herbst appliance in providing for movement of the various jaws of the patient relative to each other. A device for providing expansion of the spacing between teeth, on the same jaw level, may be seen in U.S. Pat. No. 6,036,488, on the pivotal mounting boss for mandibular and maxillary arch expander and jaw repositioner. Other related type patents can be viewed in U.S. Pat. Nos. 6,241,517, 6,402,510, 6,520,772, 6,719,557, 6,877,982, 7,094,051, and finally U.S. Pat. No. 7,500,851. As can be noted, all of these devices are for orthodontic purposes for furnishing the type of improvements to the relationship of teeth and jaws, relative to each other, in order to correct any dental malfunction.

Examples of various types of integrally structured devices for principally holding and sustaining the location of the various jaws of a patient or user, relative to each other, can be seen in a variety of other prior patents. These may be used as protecting devices, or even use for sleep apnea reduction, as can be noted in U.S. Pat. No. 3,217,705 to Roberts, on a mouth piece protector. An apparatus for the prevention of snoring and improved breathing during sleep can be seen in U.S. Pat. No. 5,427,117 to Thornton. Another anti-snoring device can be seen in U.S. Pat. No. 5,499,633 to Fenton. The patent to Roopchand, on an endotracheal tube support, is noted in U.S. Pat. No. 5,941,246, to aid the patient in breathing and during general use for routine anesthesia procedures. The patent to Lesniak, et al., U.S. Pat. No. 6,830,051, shows an interocclusal appliance. The published application to Ballwin, U.S. Patent Application Publication No. 2008/0149110, discloses an airway device, including two fixed pillars. Another published application to Ballwin, U.S. Patent Application Publication No. 2008/0149114, shows a similar device. These are examples of structural devices, generally integrally formed, to aid in maintaining the user's passage opened, for minimizing the effects of sleep apnea. Most of these prior patents and publications, as stated, show the use of integral devices for trying to alleviate sleep apnea, generally without any means for their readjustment, so as to be changeable relative to the user's jaw structure, in order to achieve maximum rearrangement of the jaws, for furnishing the most effective opening of his/her air passage, during usage and application.

Patents that show means for providing for a fixation of the teeth of the jaws of the patient, particularly with respect to the application in an oral appliance, for aiding in the realignment of teeth, can be shown in the various patents to Thornton, generally related to a dental device having an approved deformable material and method for performing same. This can be seen in U.S. Pat. No. 5,807,100 that utilizes aliphatic polyester as a deformable material for application of the user's teeth thereto, when forming the appliance. Such can also be seen in U.S. Pat. No. 6,247,926, disclosing an oral appliance having a bonding layer and methods for fitting and relining the same, during its application and usage: These types of devices are applicable for incorporating the formable material for forming a mold of impressions of some or all of the user's teeth to customize the oral appliance for and to the user's dimensions. U.S. Pat. No. 6,464,924, to the same inventor, shows a method of forming custom masks using an impression mask and applying the same type of deformable material. These are examples of the known technology to the applicants, primarily relating to orthodontic appliances, mainly for the realignment of teeth, in the first instance and generally integrated structural devices for aiding in the alleviation of sleep apnea, when applied.

The present disclosure provides further and enhanced improvements to this technology, by providing a sleep apnea device that may be adjustable, to the specifics of an individual, so as to attain and maintain, maximum airway passage, for the individual during application of this anti-snoring and sleep apnea device.

SUMMARY OF THE DISCLOSURE

This disclosure contemplates the formation of an anti-snoring and sleep apnea device, one that is not only applicable for use in the mouth of the patient or wearer, in order to alleviate apnea symptoms, but also which may be adjustable by use of a Herbst mechanism or assembly to afford its resetting in order to maximize the expansion of the airway passage for the individual user, in order to substantially reduce sleep apnea on an individual basis. Furthermore, the disclosure contemplates that application of a composition to the mandibular and maxillary trays that hold the teeth in position for both the upper jaw and the lower jaw, to assure a precise setting and maintaining of that setting of the appliance within the user's mouth and to fix that setting in its positioning of the jaws, relative to each other, during usage, so that slippage cannot occur, which, may otherwise, affect the expansion of the airway passage, during application of this device.

This anti-snoring and sleep apnea device includes a pair of polymer trays, generally that are custom fitted to provide for the application to the upper maxillary and lower mandible arrangement of teeth in the patient and user. Each one is custom designed to provide for cooperation with each other, to furnish an adjustment in the alignment of these trays, relative to each other, during their application and usage. For example, a pair of Herbst mechanisms is attached to the upper tray and to the lower tray to connect the upper tray to the lower tray in a telescoping inseparable hinged relationship to provide for mandibular advancement in fine increments on the order of one millimeter or less. Once the Herbst mechanisms are adjusted in one millimeter increments or less, the specific setting is retained and the patient may use the device.

To assure that the maxillary tray and the mandibular tray remain affixed relative to each other, when the upper and lower teeth of the patient are arranged within their respective trays, a thermal acrylic liner may be located within each of the trays and which when subjected to heat, provides for the moldability of such liner, so that when the upper and lower jaw teeth are located within their respective trays, they form an exact impression within the liner material, thus forming a complete and accurate set for the teeth, when the appliance is formed, and keeps the teeth intact within their respective trays, to prevent any slippage between these components, once the liner is formed, impressed and then set, into the precise teeth configuration within their respective liners. Hence, when the device is formed in this manner, all the patient needs to do is apply the trays to their respective teeth and then adjustment can be made to the Herbst mechanisms providing for relative shifting forwardly of the bottom tray with respect to the upper tray, until that relatively positioning of the jaws is achieved that provides better breathing for the user, in order to reduce or eliminate the effects of snoring, or apnea, during sleeping.

Generally, the polymeric upper and lower trays forming this device provide the basis for the appliance, through these preferred upper and lower trays, that can be customized for each patient's size and needs. The Herbst mechanisms that connect the upper tray to the lower tray provide for the adjustment of the lower tray relative to the upper tray to assist in maintaining the alignment of the upper and lower trays when positioned within the mouth, and preparing the trays for repositioning through adjustment by use of the Herbst mechanisms.

The device of the present disclosure comprises an intraoral device that is used for treating snoring and sleep apnea and comprises two custom fitted polymer trays, which fit over the upper and lower teeth of the patient and by use of Herbst mechanisms may orient the jaw into a predetermined relationship, that is designed to increase the patient's pharyngeal space, to thereby improve the ability of the patient to exchange air during sleeping.

The acrylic used to form the upper tray and the lower tray of the device of the present disclosure is a thermal responsive type of polymer. The material is capable of being remoldable, through thermal action, which means it eliminates the costly remaking of the appliance, after completion of any further dental work on the user. In other words, the trays may be resubjected to heat repressed against the patient's teeth, in order to furnish a more accurate realignment of the teeth, with respect to the polymer trays. The device is customized for each patient, in accordance with the device and through the usage of its adjustment mechanisms that enable the mandibular to attain an amount of advancement, generally set by the dentist or physician, at the time of its initial fitting, or when readjustment may be required. The prescribing dentist can determine the exact repositioning of the lower bit, or mandibular tray, relative to the wax construction bit obtained from the patient through the operation of the clinician initially forming the device. The dentist may also be able to fine-tune the jaw positioning, clinically, as needed by altering the Herbst mechanisms, for precise settings.

The functional relationship built into the device acts to position the lower jaw more forwardly of the upper jaw and thereby open vertically from its normal location which causes a slight protrusion of the mandible in relation to the maxilla. This forward repositioning, which is temporary while the appliance is being used, increases the pharyngeal space which assists the patient with improved air exchange, while breathing during sleep. Thus, this is the essence of the device; to provide a sleep apnea device that can be fabricated for the particular patient's mouth, having an impression of the patient's exact teeth alignment within the structured trays and then be able to undertake the fine-tuning of the lower jaw repositioning, through the manipulation and adjustment of the Herbst mechanisms incorporated into the device.

The materials used to fabricate the various components of this device include the upper and lower polymer trays, which may generally, in the preferred embodiment, be made of a methyl methacrylate. Any metal components used in the assembly of the device, such as the Herbst mechanisms and ball clasps, are generally constructed of stainless steel, so as to resist any potential for corrosion. These types of materials have a long history of safe and effective usage, in the manufacture of various dental devices, including the intraoral devices for snoring and obstructive sleep apnea that may be subjected to these types of deterioration.

The upper and lower polymeric trays for the present device, as previously described, may be made of methyl methacrylate. These trays may be obtained from a company by the name of Dentaurum, located in Ispringen, Germany.

It is also possible that the upper and lower trays may include interlinings which include a formula of aliphatic polyester, which is a form of self-curing acrylic material. This type of polyester may include a polycaprolactone polymer that may be subject to heat treatment and formation of the indentation of the patient's teeth, to provide for a precise seat for the teeth after the material has cooled and hardened, in preparation for usage within the device. This material is generally sold under the trademark THERMACRYLIC polymer and is available from Airway Management, Inc., located in Dallas, Tex. The material is a dimensionally stable polymer, yet hardens to a tough, unbreakable plastic and is remoldable when subjected to heat, as previously indicated, is non-toxic and may even soften in water. It is sold under Model Number 06-OBVS-12.

Generally, the anti-snoring and sleep apnea device is intended to reduce or eliminate night time snoring and mild to moderate obstructive sleep apnea, principally in adults. The device is worn while sleeping, to support the lower jaw in a more forwardly position, as may be prescribed by the dentist or doctor specializing in throat or sleep disorders. Obviously, the device can be readily applied by the patient and removed, as desired.

In light of the foregoing comments, it will be recognized that the present disclosure provides an anti-snoring and sleep apnea device that is adjustable to effectively shift the lower jaw of the patient more forwardly, to open and sustain the opening of the user's air passage, particularly while sleeping.

The present disclosure provides an anti-snoring and sleep apnea device that can be easily employed with highly reliable results to improve the health of the user.

The present disclosure provides an anti-snoring and sleep apnea device that incorporates an upper tray and a lower tray, for coopering with the teeth of the maxillary and mandibular, in order to provide for precise adjustment and fitting of the device when worn by the user.

The present disclosure provides an anti-snoring and sleep apnea device that incorporates an upper tray and a lower tray which each tray may include a moldable polymeric acrylic, that can be applied, in the softened state, against the teeth of the user, in order to furnish a precise impression for fixing the teeth to their respective upper and lower trays, to assure the precise and maintenance of the setting of the device when worn.

The present disclosure provides an anti-snoring and sleep apnea device that has an upper tray and a lower tray that can be adjusted and readjusted for proper positioning of forward movement to the mandibular or lower jaw of the patient during wearing of the device.

The present disclosure provides an anti-snoring and sleep apnea device that can be applied by the user and removed, or even reapplied nightly, for application in minimizing snoring and reducing sleep apnea.

The present disclosure provides an anti-snoring and sleep apnea device that can be readjusted in the teeth impressions within inner liners formed in an upper tray and a lower tray, particularly after dental work may have been performed on the patient subsequently to the original construction and setting of the device.

These and other advantages of the present disclosure will become apparent to those skilled in the art after considering the following detailed specification in conjunction with the accompanying drawings.

DETAILED DESCRIPTION OF PREFERRED EMBODIMENTS

Figure 1:
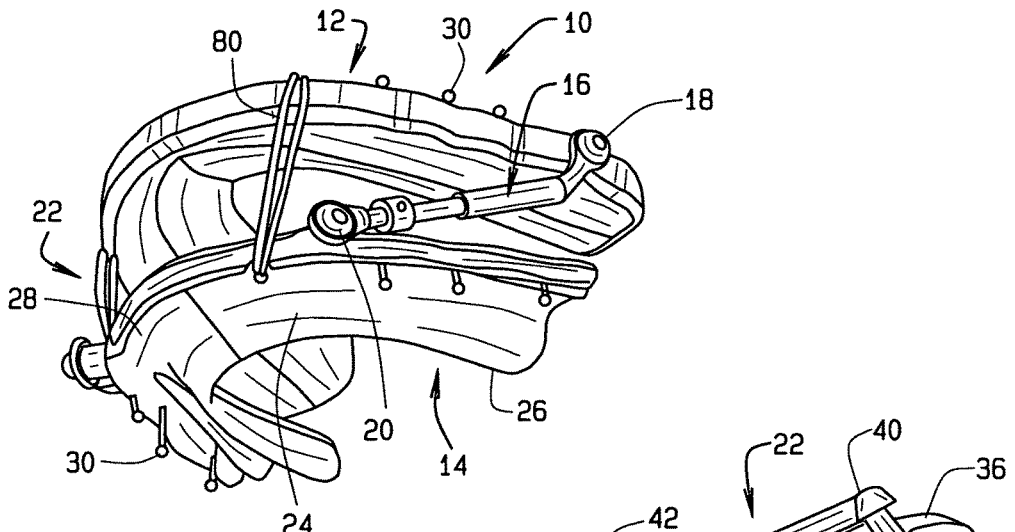
FIG. 1 is a perspective view of an anti-snoring and sleep apnea device constructed according to the present disclosure.

Referring now to the drawings, wherein like numbers refer to like items, number 10 identifies a preferred embodiment of an anti-snoring and sleep apnea device constructed according to the present disclosure. With reference now to FIG. 1, the anti-snoring and sleep apnea device 10 comprises an upper tray structure 12 and a lower tray structure 14. The upper tray structure 12 is arcuate in configuration and designed to receive the upper teeth of an individual therein. The lower tray structure 14 is also arcuate in configuration and designed to receive the lower teeth therein. A first or right Herbst mechanism 16 is attached to the upper tray structure 12 at an upper pivot 18 and is attached to the lower tray structure 14 at a lower pivot 20. Although not shown in detail in this particular view, a second or left Herbst mechanism 22 is also attached to the upper tray structure 12 and to the lower tray structure 14, as will be explained in detail further herein.

The lower tray structure 14 has an interior bottom portion 24 that is adapted for receiving the lower teeth of the user. The lower tray structure 14 also has an interior wall portion 26 and an exterior wall portion 28 with the wall portions 26 and 28 for fitting around the lower teeth of the user. The interior bottom portion 24 may have formed therein impressions or indentations for receiving the lower teeth of the user when the device 10 is positioned within the mouth of the user. The upper tray structure 12 and the lower tray structure 14 may have incorporated therein at various positions ball clasps 30. The ball clasps 30 are used to further hold or retain the device 10 to the teeth of the user when the device 10 is positioned in the mouth of the user.

Figure 2:
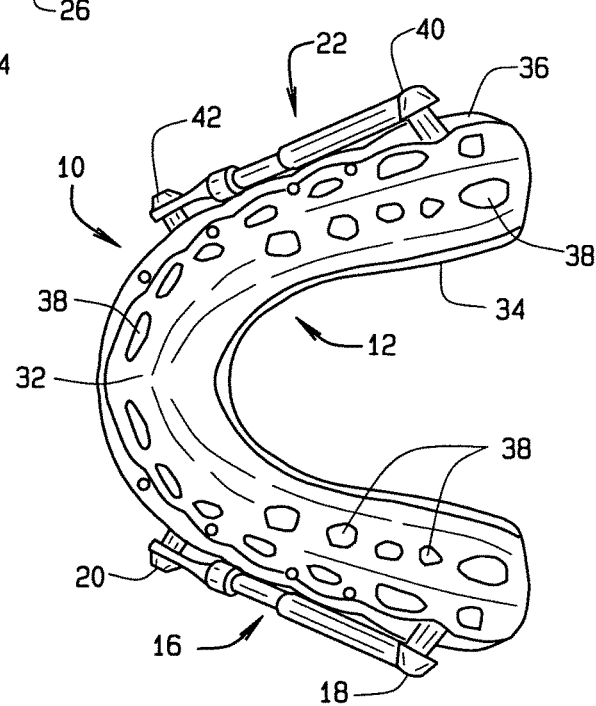
FIG. 2 is a top view of the anti-snoring and sleep apnea device constructed according to the present disclosure.

FIG. 2 is a top view of the anti-snoring and sleep apnea device 10. The upper tray structure 12 has an interior bottom portion 32 that is adapted for receiving the upper teeth of the user. The upper tray structure 12 also has an interior wall portion 34 and an exterior wall portion 36 with the wall portions 34 and 36 for fitting around the upper teeth of the user. The interior bottom portion 32 may have formed therein impressions or indentations 38 for receiving the upper teeth. The right Herbst mechanism 16 is shown being attached to the upper tray structure 12 at the upper pivot 18. The left Herbst mechanism 22 is also shown being attached to the upper tray structure 12 at an upper pivot 40. The left Herbst mechanism 22 also has a lower pivot 42. Although not shown in detail in this drawing, the lower pivot 42 is attached to the lower tray structure 14 and the lower pivot 20 of the right Herbst mechanism 22 is attached to the lower tray structure 14.

Figure 3:
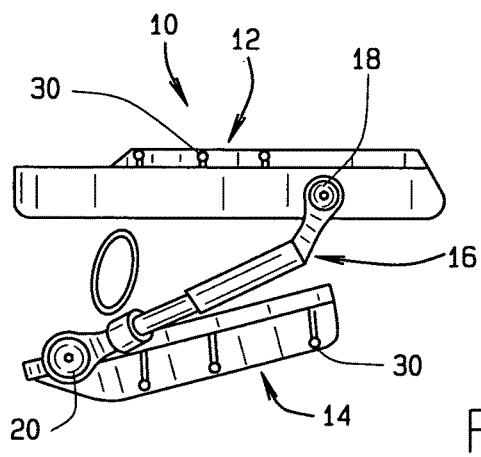
FIG. 3 is a side view of the anti-snoring and sleep apnea device constructed according to the present disclosure.

With reference now to FIG. 3, a side view of the anti-snoring and sleep apnea device 10 is depicted. The device 10 comprises the upper tray structure 12 being attached to the lower tray structure 14 by the Herbst mechanism 16. The trays 12 and 14 are held in place relative to each other by the pivots 18 and 20 of the Herbst mechanism 16 and the pivots 40 and 42 of the Herbst mechanism 22, which is not shown in this particular view. The device 10 is capable of projecting or protruding the lower jaw of the patient to a position forward to that of the upper jaw. In this arrangement, when the device 10 is worn while sleeping, a reduction in night time snoring and obstructive sleep apnea is accomplished.

Figure 4:
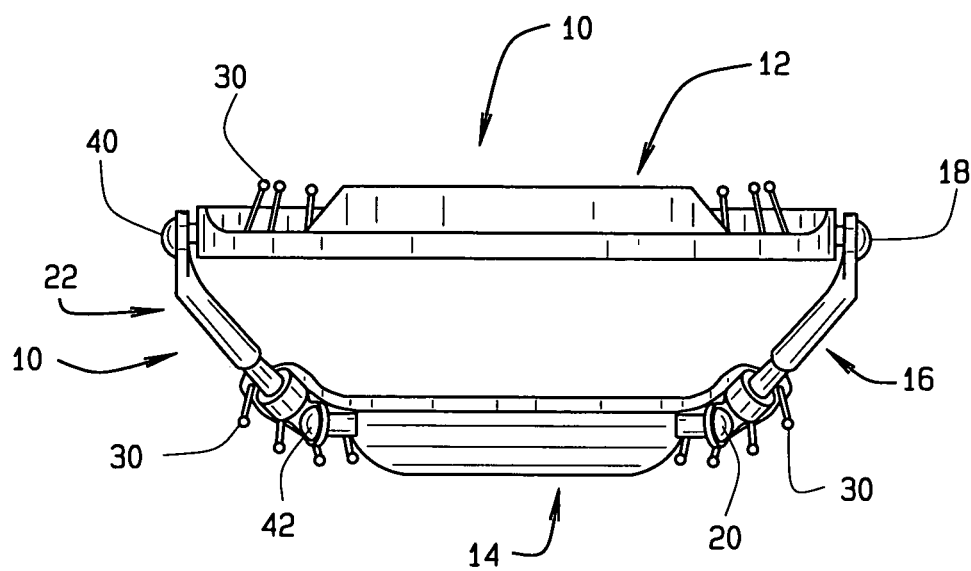
FIG. 4 is a front perspective view of the anti-snoring and sleep apnea device constructed according to the present disclosure.

FIG. 4 is a front perspective view of the anti-snoring and sleep apnea device 10. The device 10 has the upper tray structure 12 and the lower tray structure 14 connected to each other by use of the first or right Herbst mechanism 16 and the second or left Herbst mechanism 22. The right Herbst mechanism 16 has the pivot 18 embedded into the upper tray structure 12 and the pivot 20 embedded into the lower tray structure 14. The left Herbst mechanism 22 has the pivot 40 embedded into the upper tray structure 12 and the pivot 42 embedded into the lower tray structure 14. The ball clasps 30 are also shown being embedded into the trays 12 and 14.

Figure 5:
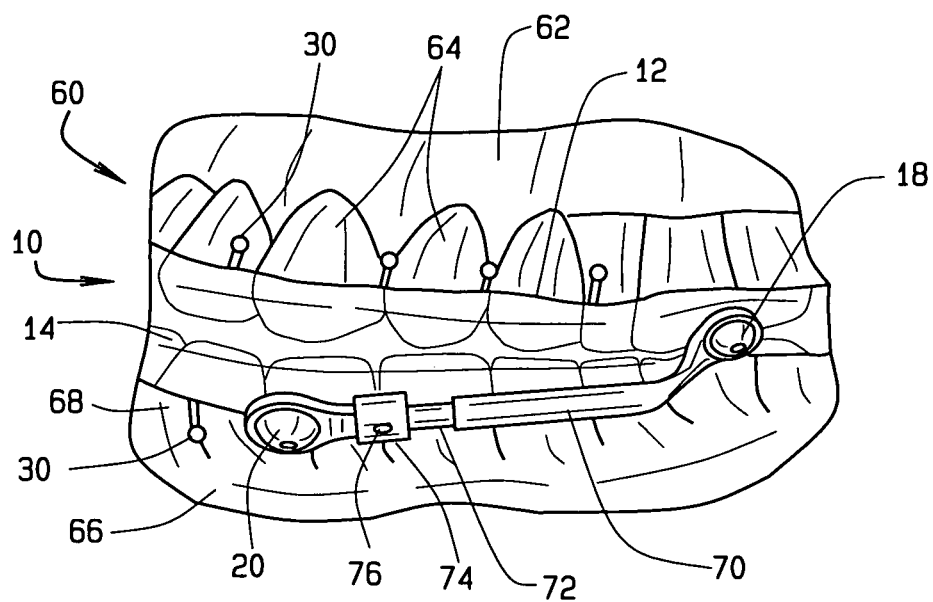
FIG. 5 is a partial side view of the anti-snoring and sleep apnea device constructed according to the present disclosure being worn by a patient.

Referring now to FIG. 5, a side view of the device 10 are illustrated being worn by a patient 60. The patient 60 has an upper jaw 62 having teeth 64 and a lower jaw 66 having teeth 68. The upper tray structure 12 is adapted to be placed over the teeth 64 and the lower tray structure 14 is adapted to be placed over the teeth 68. The ball clasps 30 are shown to fit between the teeth 64 and the teeth 68 to assist in retaining the device 10 in place.

The Herbst mechanism 16 comprises an outer tube portion 70, a movable inner rod portion 72 positioned within the outer tube portion 70, and a rotatable component 74 connected to the movable inner rod portion 72. The rotatable component 74 further includes apertures 76 that are adapted for receiving a tool, such as a wrench, to rotate the component 74. For example, a tool that may be used to advance the mechanism 16 may be a 1.5 mm Allen head wrench. By rotating the component 74, the rod portion 72 rotates relative to the outer tube portion 70 to increase or decrease the length of the Herbst mechanism 16 in a telescoping fashion. In this manner, the position of the lower jaw 66 may be positioned forward and open vertically from the normal location which causes a protrusion of the lower jaw 66 in relation to the upper jaw 62. This forward repositioning, which is temporary while the device 10 is being used, increases the pharyngeal space which assists the patient 60 with improved air exchange while sleeping. The Herbst mechanism 16 may be adjusted in increments of one millimeter or less by use of the portions 70 and 72 and the component 74. Although not shown in any detail, the Herbst mechanism 16 may include other internal components such as a spring and threads to assist in adjusting the Herbst mechanism 16. The second Herbst mechanism 22 is similar in construction and operation as that of the first Herbst mechanism 16, as just described.

A brief review of the procedure for providing an accurate fit of the upper tray structure 12 and the lower tray structure 14 of the device 10 is described as follows. First of all, the device 10 is fabricated with a thermal acrylic material. The precise fit of the teeth 64 and 68 within the trays 12 and 14 is accomplished by placing the device 10 in a hot water bath at 160° F. until the trays 12 and 14 turn clear. If too much heat is applied, the device 10 may warp. Once the trays 12 and 14 become clear, the device 10 should be quickly removed from the hot water bath and then allowed to cool for approximately thirty seconds. Following this, the trays 12 and 14 are fitted on the teeth 64 and 68 of the patient 60. In this manner, impressions are made in both of the trays 12 and 14. After about one minute, the device 10 may be removed from the mouth of the patient 60. The device 10 is then allowed to cool. Then, the device 10 should conveniently refit securely on all of the teeth 64 and 68 of the patient 60, when applied for usage. Adjustment of the device 10, through use of the Herbst mechanisms 16 and 22, will normally be done by the doctor, unless the patient 60 is clearly instructed how to perform such personally. If dental work is done on the patient 60 after initial fit of the device 10 then the just described procedure may be repeated. Further, if a doctor, dentist, orthodontist, or technician is not satisfied with the initial fitting of the device 10, then the procedure for molding the device 10 may be repeated until an accurate or desirable fit is accomplished.

Referring back to FIG. 1, an elastic band 80 is shown being placed on one of the ball clasps inserted into the upper tray structure 12 and one of the ball clasps inserted into the lower tray structure 14. The elastic band 80 may be used to ensure the position of the device 10 and for maintaining a closed position of the lower tray structure 14 relative to the upper tray structure 12.

It is also possible that the upper tray structure 12 and the lower tray structure 14 may include a quantity of a polymer compound such as thermal acrylic liner pellets. As previously discussed, polymer compound may be a formula of aliphatic polyester, which is a form of self-curing acrylic material. This type of polyester may include a polycaprolactone polymer that may be subject to heat treatment and formation of the indentation of the teeth 64 and 68 of the patient 60. Then when heat is applied to the tray structures 12 and 14 and the acrylic liner pellets, the tray structures 12 and 14 and the pellets will soften and be moldable into a precise configuration or impression of the teeth 64 and 68 of the patient 60. When the impression has been made and the tray structures 12 and 14 and the acrylic liner pellets have cooled, both the tray structures 12 and 14 will have a precise impression of the teeth 64 and 68, to provide for a very fixed setting and application of the device 10 to the teeth 64 and 68, in preparation for usage and for adjustment using the Herbst mechanisms 16 and 22.

From all that has been said, it will be clear that there has thus been shown and described herein an anti-snoring and sleep apnea device. It will become apparent to those skilled in the art, however, that many changes, modifications, variations, and other uses and applications of the subject anti-snoring and sleep apnea device are possible and contemplated. All changes, modifications, variations, and other uses and applications which do not depart from the spirit and scope of the disclosure are deemed to be covered by the disclosure, which is limited only by the claims which follow.

What is claimed is:

1. An anti-snoring and sleep apnea device comprising:
    an upper tray structure adapted to receive upper teeth of a mouth of an individual, and for locating said upper tray structure at a first position within the mouth of the individual;
    a lower tray structure adapted for receiving lower teeth of the mouth of the individual, and for locating said lower tray structure at a second position within the mouth of the individual;
    a first Herbst mechanism connected to the upper tray structure and the lower tray structure;
    a second Herbst mechanism connected to the upper tray structure and the lower tray structure, the first and second Herbst mechanisms for adjusting the second position of the lower tray structure relative to the first position of the upper tray structure during usage;
    the first Herbst mechanism comprising an upper pivot inserted into the upper tray structure and a lower pivot inserted into the lower tray structure, and said second Herbst mechanism comprising an upper pivot inserted into the upper tray structure and a lower pivot inserted into the lower tray structure;
    said first Herbst mechanism comprising an outer tube portion, a movable inner rod portion positioned within the outer tube portion, and a rotatable component operatively associated with said movable inner rod portion, and arranged exteriorly of said outer tube portion and configured to provide clear access thereto during adjustment, and said rotatable component upon loosening capable of increasing or decreasing a length of the first Herbst mechanism during usage, and said second Herbst mechanism comprising an outer tube portion, a movable inner rod portion positioned within the outer tube portion, and a rotatable component connecting with the inner rod portion and when loosened capable of increasing or decreasing a length of the second Herbst mechanism during usage, each rotatable component having an aperture for reception of an Allen wrench to fix each rotatable component upon the respective inner rod portion for increasing or decreasing the length of said first and second Herbst mechanism during adjustment, to provide for mandibular advancement in fine increments on the order of one millimeter or less during the adjustment of the Herbst mechanisms;

said first and second Herbst mechanisms comprising the upper pivot inserted into the upper tray structure and the lower pivot inserted into the lower tray structure, for pivotal securement of the Herbst mechanisms to the upper and lower tray structures during application;

said upper tray structure comprises an interior bottom portion, an interior wall portion, and an exterior wall portion with the portions adapted to receive the upper teeth of the individual;

the lower tray structure comprises an interior bottom portion, an interior wall portion, and an exterior wall portion, with the portions adapted to receive the lower teeth of the individual;

a ball clasp inserted into the upper tray structure and the lower tray structure, and an elastic band being positioned on the ball clasp inserted into the upper tray and the ball clasp inserted into the lower tray;

the upper and lower trays being formed of a polymer, and said polymer being a methyl methacrylate;

a quantity of polymer compound comprising thermal acrylic liner pellets applied to the interior bottom portions of said upper tray structure and said lower tray structure, and said acrylic liner pellets being a polycaprolactone polymer, forming an aliphatic polyester which is self-curing when subjected to heat treatment and applied against the teeth of the individual to furnish a precise impression of the teeth to furnish a very fixed setting and application of the device in preparation for usage and adjustment of the Herbst mechanisms when the device is installed during usage, and for effectively shifting the lower jaw of the patient more forwardly, to open and sustain the opening of the individual's air passage particularly while sleeping; and said acrylic liner as formed capable of remolding through thermal action for resetting of said device relative to the teeth of any individual to which the device is applied during usage.

* * * * *